US009314156B2

(12) United States Patent
Aoki

(10) Patent No.: US 9,314,156 B2
(45) Date of Patent: Apr. 19, 2016

(54) OPHTHALMOLOGIC APPARATUS AND CONTROL METHOD OF OPHTHALMOLOGIC APPARATUS

(71) Applicant: CANON KABUSHIKI KAISHA, Tokyo (JP)

(72) Inventor: Hiroshi Aoki, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/974,180

(22) Filed: Aug. 23, 2013

(65) Prior Publication Data
US 2014/0063452 A1 Mar. 6, 2014

(30) Foreign Application Priority Data

Aug. 30, 2012 (JP) ................................ 2012-189800

(51) Int. Cl.
*A61B 3/12* (2006.01)
*A61B 3/00* (2006.01)
*A61B 3/10* (2006.01)

(52) U.S. Cl.
CPC .............. *A61B 3/0091* (2013.01); *A61B 3/102* (2013.01)

(58) Field of Classification Search
CPC ....... A61B 3/102; A61B 5/0068; A61B 5/103
USPC .......................... 351/211, 221, 246, 206, 205
See application file for complete search history.

(56) References Cited

U.S. PATENT DOCUMENTS 4,279,478 A * 7/1981 Matsumura ................... 351/206
8,678,590 B2 * 3/2014 Utagawa ....................... 351/210

FOREIGN PATENT DOCUMENTS

| CN | 102038489 A | 5/2011 |
| CN | 102232824 A | 11/2011 |
| CN | 102438505 A | 5/2012 |
| JP | 2010-110392 A | 5/2010 |
| JP | 2011-024930 A | 2/2011 |
| JP | 2011-092702 A | 5/2011 |

OTHER PUBLICATIONS

Chinese Office Action issued in corresponding application No. 201310388958.8 on Feb. 13, 2015.

* cited by examiner

*Primary Examiner* — Hung Dang
(74) *Attorney, Agent, or Firm* — Carter, DeLuca, Farrell & Schmidt, LLP

(57) ABSTRACT

This invention provides an ophthalmologic apparatus that requires no fixation line control instruction by an operator to a patient even when executing an inspection set including a plurality of scanning conditions. In an ophthalmologic apparatus including a scanning unit configured to scan measuring light on an eye to be inspected and execute measurement of the eye to be inspected, and a fixation unit configured to fixate the eye to be inspected to a desired measurement position, a determination unit configured to determine whether to cause the scanning unit to continue the measurement of the eye to be inspected in accordance with an inspection set, and a fixation target control unit configured to change the on state of the fixation unit when the determination unit has determined to continue the measurement are arranged.

19 Claims, 8 Drawing Sheets

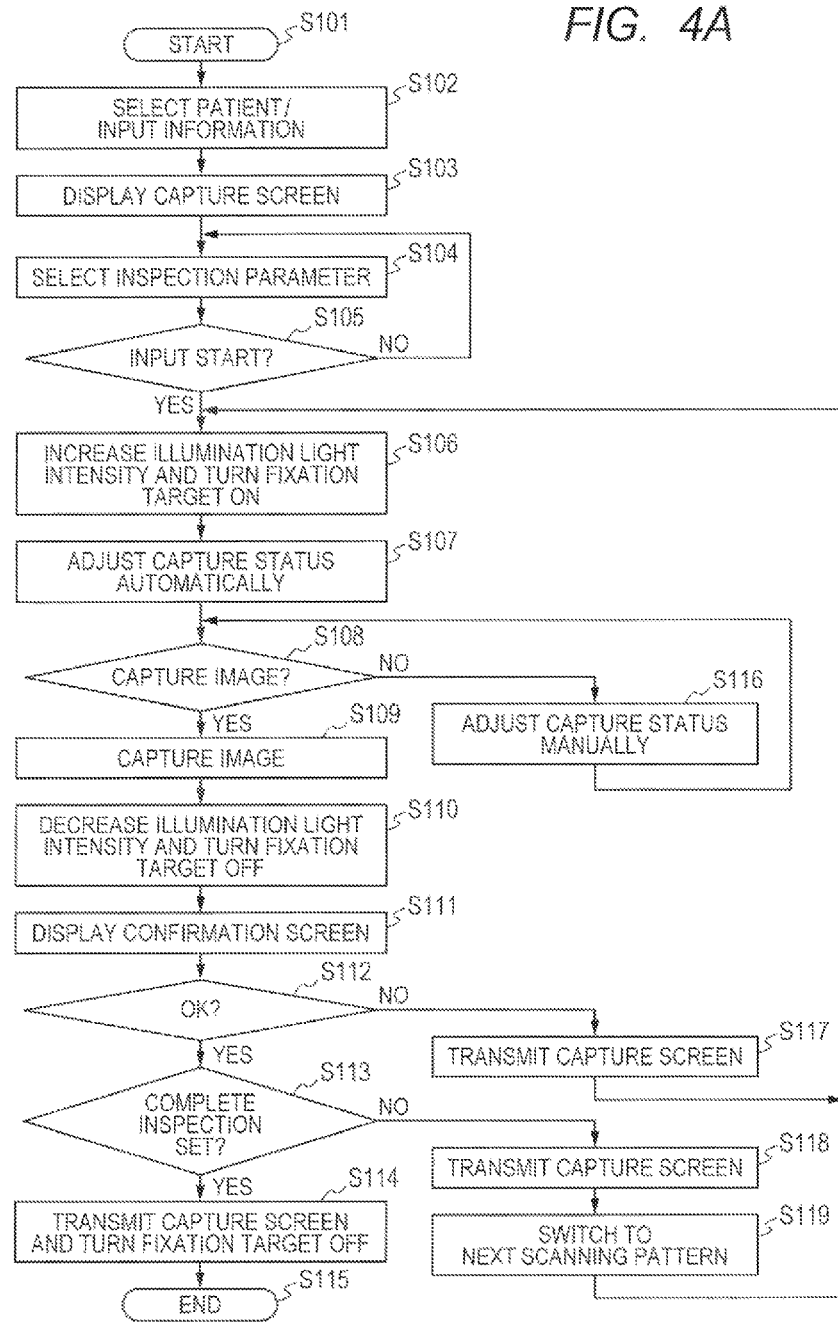

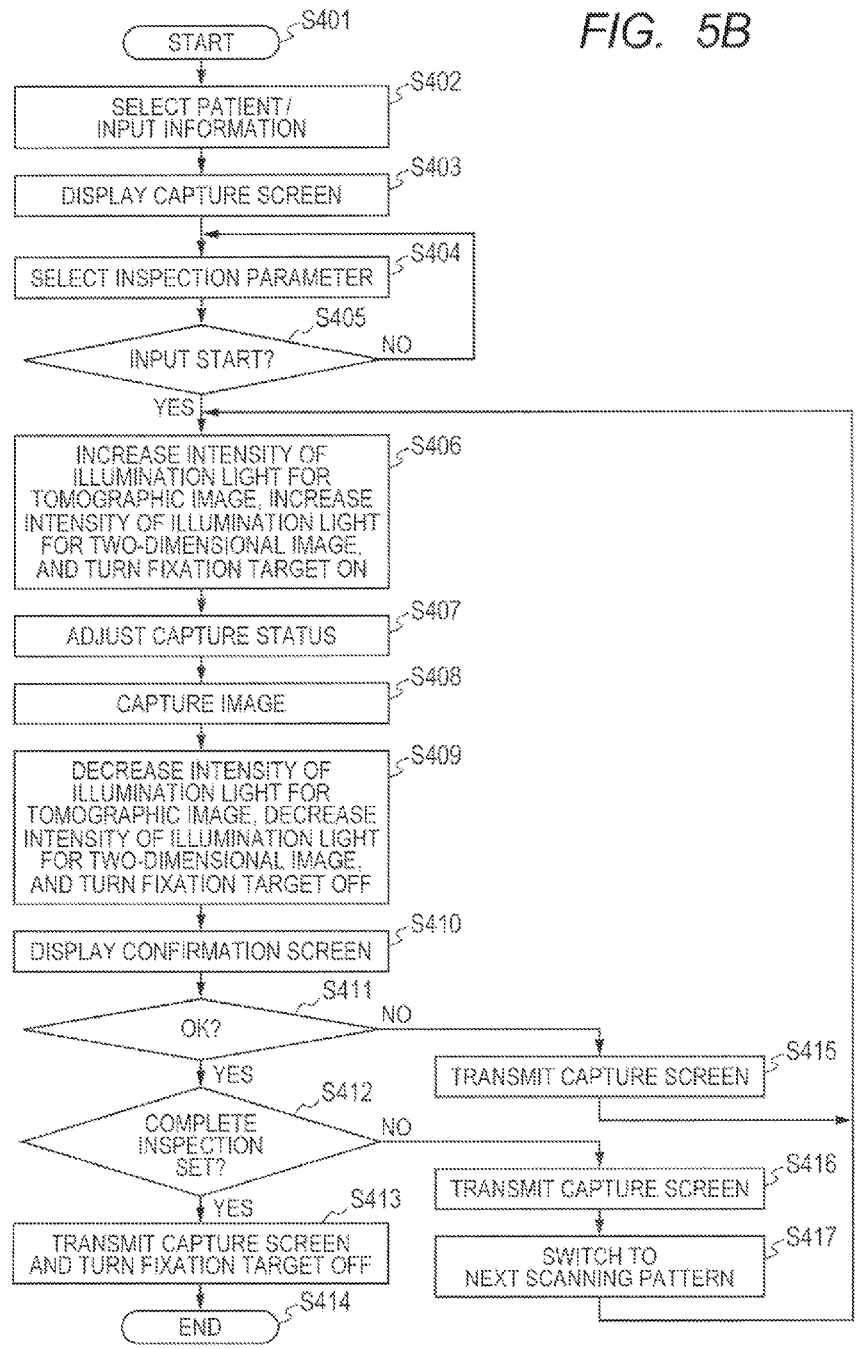

OPHTHALMOLOGIC APPARATUS AND CONTROL METHOD OF OPHTHALMOLOGIC APPARATUS

BACKGROUND OF THE INVENTION

1. Field of the Invention

The present invention relates to an ophthalmologic apparatus for imaging and measuring an eye to be inspected and a control method of the ophthalmologic apparatus.

2. Description of the Related Art

Currently, various ophthalmologic devices using optical devices are used. For example, various devices are used as an optical device for observing an eye, including an anterior ocular segment imaging apparatus, a fundus camera, and an SLO (Scanning Laser Ophthalmoscope). Particularly, an optical tomography apparatus based on OCT (Optical Coherence Tomography) using multiple wavelength interference can obtain a high-resolution image of a sample and is becoming an indispensable ophthalmologic device in a clinic specialized to retinal diseases. This apparatus is used not only in ophthalmology but also in an endoscope or the like. This will be referred to as an OCT apparatus hereinafter.

The OCT apparatus can measure the slices of an object to be inspected by dividing measuring light that is low-coherent light into reference light and measuring light, illuminating the object to be inspected with the measuring light, and causing the reference light and return light from the object to be inspected to interfere with each other. The OCT apparatus can also obtain a high-resolution tomographic image by scanning the measuring light on a sample. The OCT apparatus can obtain a tomographic image of the retina on the fundus of an eye to be inspected, and is therefore widely used in ophthalmologic diagnosis of the retina and the like.

The OCT apparatus acquires a two-dimensional tomographic image by one-dimensionally scanning measuring light on a specific region, and acquires a three-dimensional image by repetitively acquiring the two-dimensional tomographic image while shifting its position. To reduce the influence of noise generated irregularly, the OCT apparatus adds a plurality of images captured in the same region and calculates the average value, of pixel values (see Japanese Patent Application Laid-Open No 2010-110392).

As described above, the ophthalmologic apparatus needs to acquire tomographic images in various scanning patterns for various parts of the eye to be inspected.

On the other hand, Japanese Patent Application Laid-Open No. 2011-024930 discloses an OCT apparatus that prepares a plurality of scanning patterns in advance for each morbid portion. It is therefore possible to obtain an appropriate tomographic image for each portion of the eye to be inspected. In addition, Japanese Patent Application Laid-Open No. 2011-092702 discloses an OCT apparatus that performs inspection using a plurality of scanning patterns while conforming the state of a morbid portion. This makes it possible to roughly capture and confirm the whole fundus of the eye to be inspected in the first scanning cycle and decide the part of interest and after that perform more specific imaging.

The OCT apparatus generally performs inspection using a plurality of scanning patterns, as described above. This will be referred to as an inspection set. The inspection set is repetition of measurement and imaging result confirmation. An OCT apparatus capable of more smoothly performing inspection even during measurement is demanded.

In the ophthalmologic apparatus disclosed in Japanese Patent Application. Laid-Open No. 2010-110392 or 2011-024930, however, no method of fixating the eye to be inspected during transition to the next inspection pattern in the inspection set is disclosed.

In the ophthalmologic apparatus disclosed in Japanese Patent Application Laid-Open No. 2011-092702, the fixation target is set in every inspection, though no method of fixating the eye to be inspected during transition to the next inspection pattern in the inspection set is disclosed. The operator needs to instruct fixation line control of the eye to be inspected every time the next inspection pattern starts.

As described above, the operator needs to give consideration to make measurement smoothly progress even during the time after the end of one pattern inspection to The next pattern inspection in the inspection set.

SUMMARY OF THE INVENTION

The present invention has been made in consideration of the above-described problem, and provides an ophthalmologic apparatus capable of smoothly causing transition to the next inspection pattern in an inspection set and efficiently executing the inspection while reducing the burden on the operator and the patient.

An ophthalmologic apparatus according to the present invention comprises: a scanning unit configured to scan measuring light on an eye to be inspected and execute measurement of the eye to be inspected; a fixation unit configured to fixate the eye to be inspected to a desired measurement position; a determination unit configured to determine whether to cause the scanning unit to continue the measurement of the eye to be inspected; and a fixation target control unit configured to change an on state of the fixation unit when the determination unit has determined to continue the measurement of the eye to be inspected.

A control, method of an ophthalmologic apparatus according to the present invention comprises: causing a fixation unit to fixate an eye to be inspected to a desired measurement position; scanning measuring light on the eve to be inspected and executing measurement of the eye to be inspected; determining whether to continue the measurement of the eye to be inspected; and changing an on state of the fixation unit upon determining to continue the measurement of the eye to be inspected.

According to the ophthalmologic apparatus of the present invention, since the patient can automatically be caused to fixate the eye during an inspection set, it is possible to reduce the burden on the patient without applying a burden on the operator. It is also possible to reduce operations of requesting the patient to fixate the eye and improve the usability.

Further features of the present invention will become apparent from the following description of exemplary embodiments with reference to the attached drawings.

BRIEF DESCRIPTION OF THE DRAWINGS

FIGS. 4A and 4B are explanatory views showing operation procedures according to modifications of the first embodiment.

FIG. 5B is an explanatory view of an operation procedure.

DESCRIPTION OF THE EMBODIMENTS

First Embodiment

The first embodiment of the present invention will be described with reference to the accompanying drawings.

(Arrangement of Main Body)

Figure 1A:
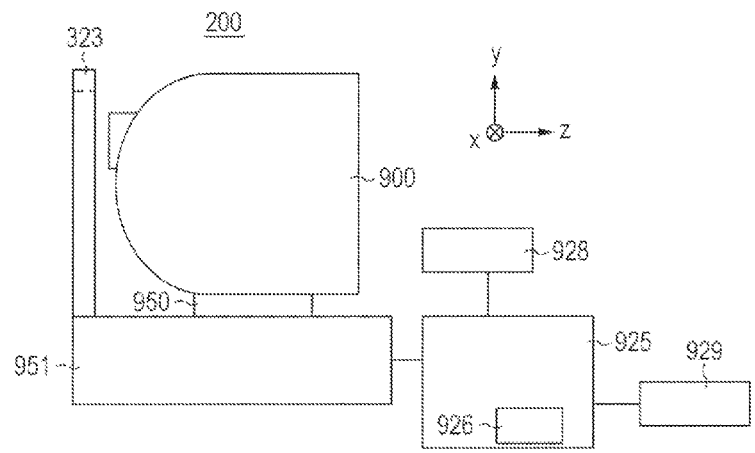
FIGS. 1A and 1B are explanatory views of an ophthalmologic apparatus according to the first embodiment.

FIG. 1A is a side view of an ophthalmologic apparatus according to the first embodiment. Reference numeral 200 denotes an ophthalmologic apparatus. An inspection unit 900 is a measurement optical system configured to acquire an anterior ocular image, and a two-dimensional image and a tomographic image of a fundus. A stage unit 950 can move the inspection unit in the X, Y, and Z directions using a motor (not shown). A base unit 951 incorporates a spectroscope to be described later.

A personal computer 925 serves as a control unit of the inspection unit and the stage unit. The personal computer 925 not only controls the stage unit but also constructs a tomographic image to be described later and switches the inspection set. A hard disk 926 serves as a patient information storage unit, an inspection set storage unit, and a scanning control unit, and stores a tomography imaging program and the like. A monitor 928 serves as a display unit. An input unit 929 inputs an instruction so the personal computer and more specifically, includes a keyboard and a mouse. A face rest 323 fixes the chin and forehead of a patient, thereby prompting to fix the eye of the patient.

(Arrangements of Measurement Optical System and Spectroscope)

The arrangements of the measurement optical system and the spectroscope according to this embodiment will be described with reference to FIG. 1B.

The internal arrangement of the inspection unit 900 will be explained first. An objective lens 135-1 is set to face an eye 107 to be inspected. A first dichroic mirror 132-1 and a second dichroic mirror 132-2 are arranged on the optical axis. The dichroic mirrors branch the optical path into an optical path 351 of an OCT optical system, an optical path 352 for fundus observation and the fixation target, and an optical path 353 for anterior ocular observation on the wavelength band basis.

A third dichroic mirror 132-3 further branches the optical path 352 into an optical path to a CCD 172 for fundus observation and an optical path to a fixation target 191 similarly on the wavelength band basis. Reference numerals 135-3 and 135-4 denote lenses. The lens 135-3 is driven by a motor (not shown) to focus for the fixation target and fundus observation. In the present invention, the fixation target 191 functions as a fixation unit that fixates the eye to be inspected to a desired measurement position. The CCD 172 has the sensitivity near the wavelength of fundus observation illumination light (not shown), more specifically, near 780 nm. On the other hand, the fixation target 191 generates visible light and prompts the patient to fixate the eye.

Reference numeral 135-2 denotes a lens on the optical path 353; and 171, an infrared COD for anterior ocular observation. The CCD 171 has the sensitivity near the wavelength of anterior ocular observation illumination light (not shown), more specifically, near 970 nm.

The optical path 351 forms the OCT optical system, as described above, which captures a tomographic image of The fundus of the eye 107 to be inspected. More specifically, the OCT optical system obtains an interference signal to form a tomographic image. An XY scanner 134 is configured to scan light on the fundus. Although the XY scanner 134 is illustrated as one mirror, it scans in two, x- and y-axis directions. In the present invention, the XY scanner 134 and a component that controls the XY scanner function as a scanning unit that scans measuring light on the eye to be inspected and executes measurement of the eye to be inspected. A shutter 140 can be inserted into or retreated from the optical path 351 by a driving unit (not shown). Reference numerals 135-5 and 135-6 denote lenses. The lens 135-5 is driven by a motor (not shown) to focus light from an OCT light source 101, which exits from a fiber 131-2 connected to photocoupler 131, onto the fundus 107. With this focusing, the light from the fundus 107 simultaneously forms a spot image on the distal end of the fiber 131-2 and enters.

The arrangements of the optical path for the OCT light source 101, a reference optical system, and the spectroscope will be described next.

Reference numeral 101 denotes the OCT light source; 132-4, a mirror, 115, dispersion compensation glass; 131, the above-described photocoupler; 131-1 to 131-4, single-mode optical fibers integrally connected to the photocoupler; 135-7, a lens, and 180, a spectroscope.

These components form a Michelson interference system. Light emitted by the OCT light source 101 passes through the single-mode optical fiber 131-1 and the photocoupler 131 and is divided into measuring light on the side of the optical fiber 131-2 and reference light on the side of the optical fiber 131-3.

The measuring light passes through the optical path of the above-described OCT optical system, illuminates the fundus of the eye 107 to be inspected which is the observation target, and arrives at the photocoupler 131 through the same optical path due to reflection and scattering by the retina. The reference light that has exited from the optical fiber 131-3 is reflected by the mirror 132-4 and arrives at the photocoupler 131 through the same optical path.

The photocoupler 131 combines de measuring light and the reference light to form interference light. In this case, interference occurs when the optical path length of the measuring light and that of the reference light have become almost equal. The mirror 132-4 is held to be adjustable in the optical axis direction by a motor and a driving mechanism. (neither are shown), and can adjust the optical path length of the reference light to the optical path length of the measuring light which changes depending on the eye 107 to be inspected. The interference light is guided to the spectroscope 180 through the optical fiber 131-4.

A deflection adjustment unit 139-1 is provided on The measuring light side in the optical fiber 131-2. A deflection adjustment unit 139-2 is provided on the reference light side in the optical fiber 131-3. Each of the deflection adjustment units includes several, parts where the optical fiber looped. Each deflection adjustment unit can adjust the deflection state of the measuring light and that of the reference light by making the looped portions pivot about the longitudinal direction of the fiber and thus twisting the fiber.

The spectroscope 180 is formed from lenses 135-8 and 135-9, a diffraction grating 181, and a line sensor 182.

The interference light that has exited from the optical fiber 131-4 is converted into a parallel beam through the lens 135-8 and divided by the diffraction grating 181, and forms an image on the line sensor 182 through the lens 135-9.

The periphery of the OCT light source 101 will be described next. The OCT light source 101 is an SLD (Super Luminescent Diode) that is a typical low-coherent light source. The center wavelength is 855 nm, and the wavelength bandwidth is about 100 nm. The bandwidth is an important parameter because it influences the resolution of an obtained tomographic image in the optical axis direction. As the type of the light source, SLD is selected here. However, ASE (Amplified Spontaneous Emission) or the like is also usable as long as it can emit low-coherent light. As for the center wavelength, near infrared light can suitably be used in consideration of measurement of an eye. The center wavelength influences the resolution of an obtained tomographic image in the lateral direction, and is therefore preferably as short as possible. For these reasons, the center wavelength is set to 855 nm.

In this embodiment, a Michelson interference system is used as an interference system. However, a Mach-Zehnder interference system may be used. If the light intensity difference between the measuring light and the reference light is large, a. Mach-Zehnder interference system is preferably used. If the light intensity difference is relatively small, a Michelson interference system is preferably used.

(Tomographic Image Capturing Method)

A tomographic image capturing method using the ophthalmologic, apparatus 200 will be described. The ophthalmologic apparatus 200 can capture a tomographic image of a predetermined part of the eye 107 to be inspected by controlling the XY scanner 134.

Figure 1B:
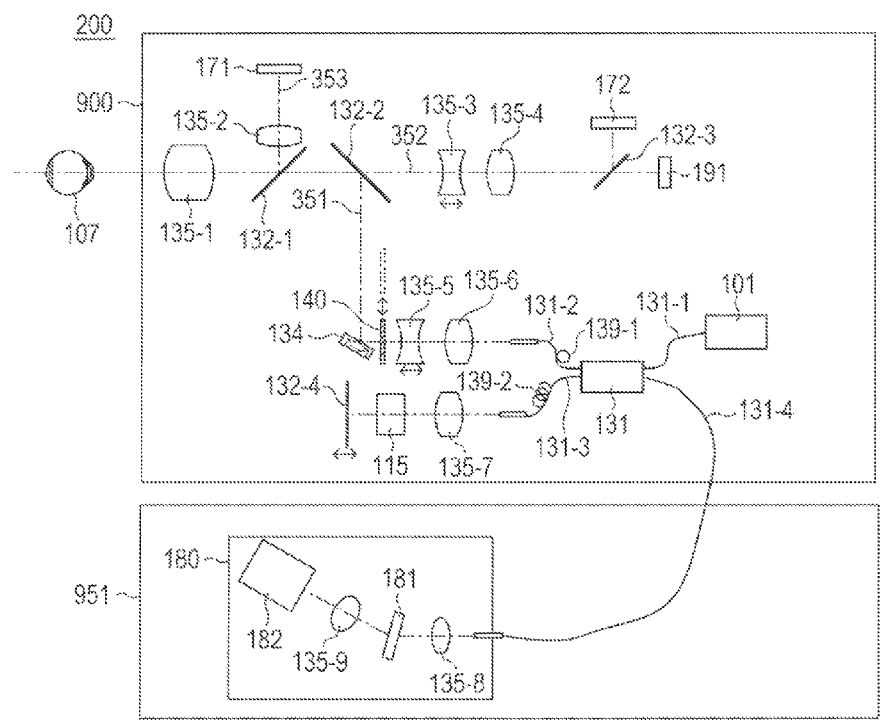

First, the measuring light is scanned in the X direction in FIGS. 1A and 1B, and the line sensor 182 captures the information of a predetermined number of lines within the X-direction image capturing range on the fundus. A luminance distribution on the line sensor 182 obtained at a certain position in the X direction undergoes FFT (Fast Fourier Transform). The linear luminance distribution obtained by FFT is converted, into density or color information to be displayed on the monitor 928. This is called an A scan image. A two-dimensional image obtained by arranging a plurality of A scan images is called a B scan image. After a plurality of A scan images used to construct one B scan image are captured, the scanning value in the Y direction is moved, and scanning in the X direction is performed again, thereby obtaining a plurality of B scan images.

The plurality of B scan images or a three-dimensional image constructed by the plurality of B scan images is displayed on the monitor 928 and used by the operator for diagnosis of the eye to be inspected.

In the above-described example, the B scan image is obtained by scanning in the X direction. However, the present invention is not limited to this The B scan image may be obtained by scanning in the Y direction. Alternatively, the B scan image may be obtained by forming an arbitrary scanning pattern by scanning in both the X direction and the Y direction.

(Arrangement of Inspection Set)

An inspection set will be explained next. Scanning patterns are formed by a variety of loci of, for example, line scan, cross line scan, plural line scan, circle scan, and radial scan. To appropriately inspect various kinds of morbid portions, an appropriate scanning pattern needs to be decided out of them. Some morbid portions need to be inspected using a plurality of scanning patterns.

A scanning pattern storage unit in the personal computer 925 stores, in advance, scanning patterns suitable for morbid portions to be inspected. In correspondence with, for example, macular diseases, 3D scan and horizontal/vertical cross scan for scanning an entire region are stored. In correspondence with papilla diseases, horizontal line scan, circle scan, and the like are stored. The personal computer 925 includes a module area functioning as an inspection set unit that reads out an inspection set associated with measurement information to execute a plurality of scanning conditions stored in the hard disk 926 and causes the scanning unit to execute the measurement.

When scanning patterns suitable for each morbid portion are prepared in advance, as described above, inspection suitable for each of various kinds of morbid portions can be performed. In addition, the operator needs only select an appropriate inspection set from the prepared inspection sets. This can save the operator time and improve the throughput.

(Arrangement of Capture Screen)

Figure 2A:
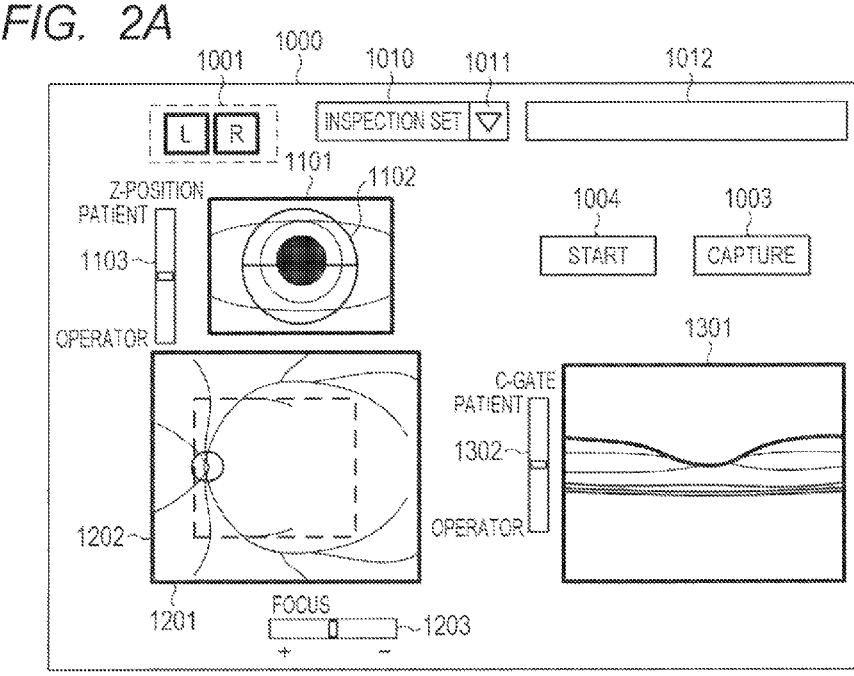
FIG. 2A is an explanatory view of a capture screen according to the present invention.

The capture screen (to be described later) according to this embodiment will be described with reference to FIG. 2A. The capture screen is a screen to do various kinds of settings and adjustment to obtain a desired image of an eye to be inspected. This screen is displayed on the monitor 928 before image capturing.

Reference numeral 1101 denotes an anterior ocular observation screen obtained by the CCD 171 for anterior ocular observation; 1201, a two-dimensional fundus image display screen obtained by the CCD 172 for fundus observation; and 1301, a tomographic image display screen used no confirm an acquired tomographic image.

Reference numeral 1001 denotes buttons to switch left-right eyes to be inspected. The operator presses the L or R button to move the inspection unit 900 to the initial position for she left or right eye.

An inspection set selection screen 1010 displays a selected inspection set. To change the inspection set, the operator clicks 1011 to display a pull-down menu (not shown) and selects a desired inspection set. A scanning pattern display screen 1012 displays the outline of a scanning pattern, for example, horizontal scan, vertical scan, or cross scan to be executed in the currently selected inspection set.

The operator clicks on an arbitrary point on the anterior ocular observation screen 1101 to move the inspection unit and locate the point at the center of the screen, thereby aligning the inspection unit and the eye to be inspected.

Acquisition of a two-dimensional image and a tomographic image starts upon pressing a start button 1004. The acquired images of the eye to be inspected are displayed on the two-dimensional fundus image display screen 1201 and the tomographic image display screen 1301 in real time.

Sliders arranged near the images are used to do adjustment. A slider 1103 adjusts the Z-direction position of the inspection unit with respect to the eye to be inspected. A slider 1203 is used to perform focusing adjustment. A slider 1302 is used to adjust the position of the coherence gate. Focusing adjustment is performed to move the lenses 135-3 and 135-5 in the illustrated directions to adjust the in-focus state of the fundus. Coherence gate adjustment is performed to move the mirror 132-4 in the illustrated directions to observe the tomographic image at a desired position on the tomographic image display screen. With these adjustment operations, the operator creates a state to perform optimum image capturing.

After the various kinds of adjustment have been done, an image capturing button 1003 is pressed to perform desired image capturing.

(Arrangement of Tomographic Image Display Screen)

Figure 2B:
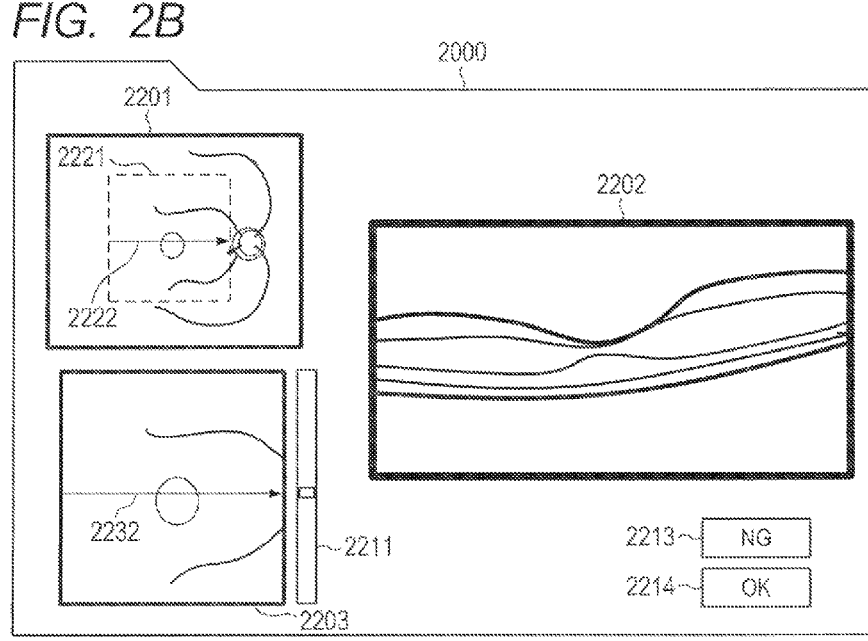
FIG. 2B is an explanatory view of a confirmation screen.

A confirmation screen (to be described later) according to this embodiment will be described next with reference to FIG. 2B. The confirmation screen is a screen displayed on the monitor 928 after image capturing. The operator confirms whether the captured tomographic image includes an imaging error. In addition, a morbid portion and the like are confirmed such that they can be used to judge the part of interest in the next image capturing.

Reference numeral 2201 denotes a two-dimensional fundus image display screen obtained by the CCD 172 for fundus observation; 2202, a tomographic image display screen used to confirm the acquired tomographic image; 2203, a screen (to be referred to as a C scan screen hereinafter) that displays a fundus image reconstructed from acquired tomographic images; 2211, a slider used to designate a sectional position of the tomographic image displayed on the tomographic image display screen; 2213, an NG button on which the mouse button or the like is clicked when the operator has judged the acquired tomographic image as an imaging error; and 2214, an OK button on which the mouse button or The like is clicked when the operator has judged the acquired tomographic image not as an imaging error but as excellent.

The two-dimensional fundus image display screen 2201 includes a tomographic image acquisition range 2221 and an arrow 2222 indicating the position and scanning direction, in the tomographic image acquisition range, of the tomographic image displayed in the tomographic image display screen 2202. Similarly, the C scan screen 2203 includes an arrow 2232 indicating the position and scanning direction, in the tomographic image acquisition range, of the tomographic image displayed in the tomographic image display screen 2202.

In the initial state, the tomographic image display screen 2202 displays the tomographic image at the center position of the tomographic image acquisition range 2221. To more finely check each tomographic image, the operator manipulates the slider 2211. The tomographic image displayed on the tomographic image display screen 2202 thus moves within the tomographic image acquisition range. Hence, the operator can check all tomographic images. The operator can accurately check whether a tomographic image is an imaging error and roughly confirm a morbid portion and she like.

(Operation Procedure)

Figure 3:
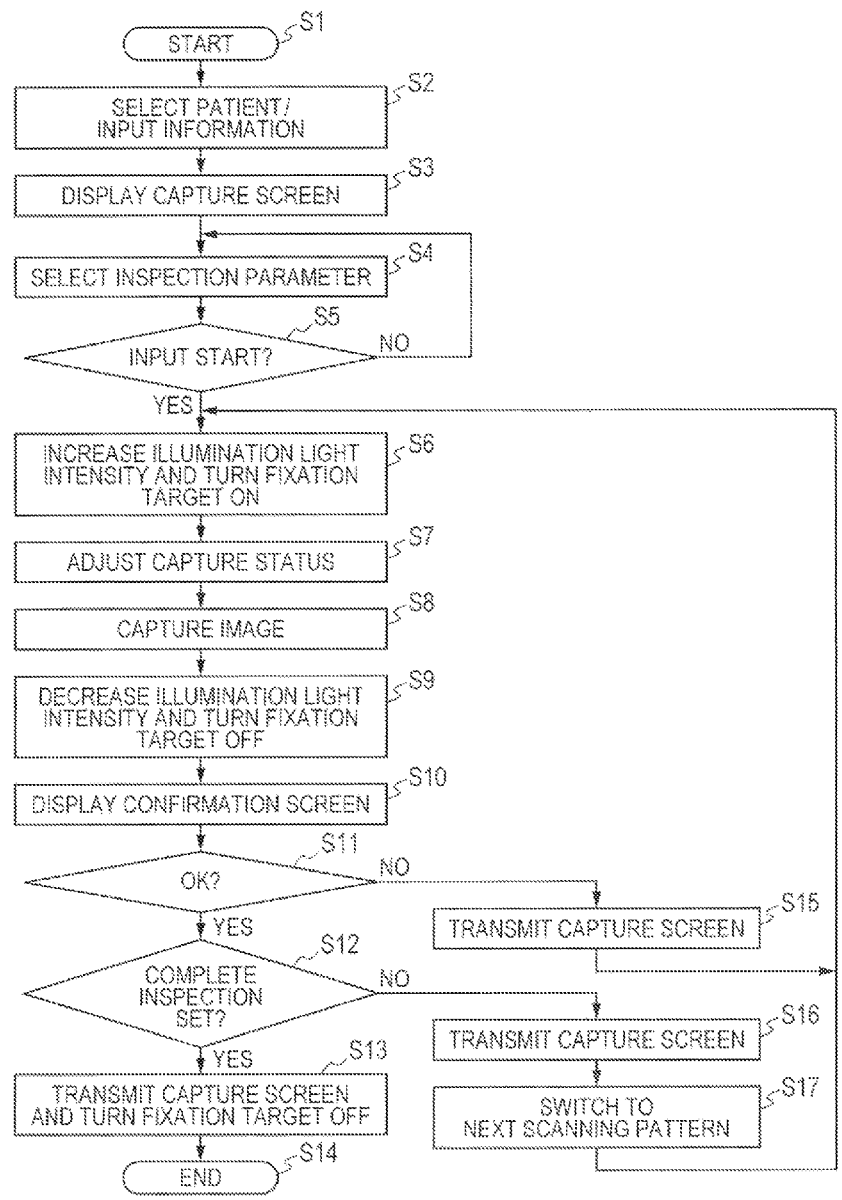
FIG. 3 is an explanatory view of an operation procedure according to the first embodiment.

The operation procedure of image capturing according to this embodiment will be described with reference to FIG. 3.

When inspection starts in step S1, the personal computer 925 executes the inspection program. In step S2, a patient information input screen is displayed on the monitor 928. The operator selects a patient or, in first medical examination, inputs patient information. The process advances to step S3 by the operation (for example, mouse button clicking on the OK button displayed on the patient information input screen) of the operator.

In step S3, the monitor 928 displays the above-described capture screen 1000 and waits for inspection parameter input by the operator.

In step S4, the operator clicks on, for example, the buttons of the capture screen 1000 in the inspection parameter input waiting state, thereby selecting the left or right eye to be inspected and the inspection set.

When the operator selects (clicks) the start button 1004 in step S5, the process advances to step S6. If the start button 1004 is not selected, the process returns to the inspection parameter input waiting state (step S4).

In step S6, the fixation target 191 is turned on to fixate the eye to be inspected and perform fixation line control as first fixation line control, and the measuring light intensity is increased to set a capture enable state. More specifically, the OCT scanner 134 starts scanning based on the scanning pattern corresponding the inspection set set in step S4 and prepared in the inspection set storage unit of the personal computer 925 in advance. In addition, the OCT light source 101 increases the emission light intensity from an of state or a low light intensity state to a capture enable level. The OCT shutter 140 retreats from the optical path. This allows the measuring light of to capture enable level to enter the eve to be inspected. The process advances from step S6 to step S7.

In step S7, the previews of the acquired fundus image and tomographic image are displayed in the capture screen 1000 on the monitor, and various kinds of adjustment are performed based on the pieces of information to obtain an optimum capture status. More specifically, XYZ adjustment is performed based on the image of the anterior ocular segment of the eye to be inspected obtained by she COD 171 for anterior ocular observation so that the inspection unit is located at an optimum position with respect to the eye to be inspected. Simultaneously, adjustment of the optical path length of the reference light path by movement of the mirror 132-4, focusing of the fundus image by the lens 135-3, and focusing of the tomographic image by the lens 135-5 are performed. With this operation, the state of die apparatus is set in a state optimum for image capturing of the eye inspected. After the adjustment of this step, the process advances to step S8. The process may advance to step S8 when the operator has clicked the mouse button or the like on the image capturing button 1003 on the above-described capture screen 1000, or automatically advance to step S8 when the various kinds of adjustment are completed.

In step S8, first image acquisition is performed to capture a tomographic image using the scanning pattern based on the inspection set selected in step S4. Simultaneously, the tomographic image and the fundus image acquired by the CCD for fundus observation are saved in the storage device of the personal computer 925. After that, the process automatically advances to step S9.

In step S9, since image capturing has already ended, the light entering the patient is reduced. More specifically, the OCT shutter 140 is inserted into the optical path, and the OCT light source 101 is turned off, or the emission light intensity is decreased. In addition, the operation of the OCT scanner 134 is stopped at an arbitrary position. Furthermore, the fixation target 191 may be blinked to notify the patient of the end of measurement. Note that this blinking is done only for a predetermined period or ended until scanning pattern switching is performed in step S17 to be described later. The patient may be notified by causing the fixation target 191 to not blink but reduce the light intensity or change the size or color. After that, the process automatically advances to step S10. In this case, the OCT scanner 134 may continuously be driven at a lower scanning speed, instead of being stopped. This makes it possible to reduce the unnecessary driving power and also reduce the unnecessary driving sound.

In step S10, the monitor displays a confirmation screen 2000 as described above. The operator confirms each tomographic image and judges the presence/absence of an imaging error in consideration for example, the presence/absence of a morbid portion and the part to place focus at the next time of image capturing, as described above. Since this judgment may take a long time, the burden on the patient can be reduced by decreasing the intensity of light illuminating the patient in step S9.

Next, the process advances step S11. The operator selects the presence/absence of an imaging error. If the tomographic image is not an imaging error, the operator clicks the mouse button or the like on the OK button 2214 in the above-described confirmation screen 2000, and the process advances to step S12. On the other hand, if the tomographic image is an imaging error, the operator clicks on the NG button 2213, and the process advances to step S15.

When she process has advanced to step S15, the screen displayed on the monitor is switched from the confirmation screen to the capture screen, and the process returns to step S6. Since the contents displayed on the monitor are automatically appropriately transited to those suitable for the situation in the above-described way, the operator can perform a comfortable operation on a single monitor. In addition, since the acquired image of the eye to be inspected can be displayed largely on the single monitor, the adjustment operation or image confirmation can easily be done. Note that when the process has returned from step S15 to step S6, the fixation target need not be turned on again in step S6 because it is already on.

In step S12, it is judged whether the measurement based on the scanning pattern, for example, the first scanning condition stored in the inspection set set in step S4 is wholly completed or whether to continue the measurement. This judgment is executed by a module area in the personal computer 925 serving as a control, unit, which functions as a determination unit that determines whether the scanning unit continues the measurement of the eye to be inspected. If all the scanning patterns to be inspected are completed, the process advances to step S13. On the other hand, if measurement by the scanning unit based on a scanning pattern to be inspected, for example, the second scanning condition next to the first scanning condition remains, and the judgment unit has judged to start the measurement, the process advances to step S16. Note that the above-described inspection set unit also functions as a scanning condition change unit that changes the scanning condition of measuring light by the scanning unit, and changes the scanning condition from the first scanning condition to the second scanning condition.

When the process has advanced to step S16, the judgment unit judges to continue the measurement of the eye to be inspected. The display unit 928 switches the screen display from the confirmation screen 2000 to the capture screen 1000, and the process advances to step S17.

In step S17, the scanning control unit reads out the second scanning condition that is the next scanning pattern predetermined in the inspection set selected in step S4, and sets the second scanning condition as the scanning pattern for the net scanning of the OCT scanner 134. After that, the process returns to step S6. The eye to be inspected is fixated by second fixation line control. The OCT scanner 134 automatically starts scanning based on The scanning pattern set in step S17. Second image acquisition is thus performed for the eye to be inspected fixated by the second fixation line control. The OCT light source 101 is turned on, and the OCT shutter 140 retreats from the optical path. Note that the above-described turn-on of the fixation target and first and second fixation line control are executed by a module area functioning as a fixation target control unit in the personal computer 925, which controls The fixation target 191. Note that when the process has returned from step S17 to step S6, the fixation target need not be turned on anew because it is already on. To switch the fixation on position in accordance with the inspection condition read out in step S17, the on position of the fixation target 191 is changed in step S17. Note that the personal computer 925 serving as the control unit reads out the inspection set and controls the OCT scanner 134 in accordance with the readout inspection set in the above-described way. During the time from step S8 to step S17, that is, during the time from image capturing under the first condition to image capturing under the second condition, the light intensity of the fixation target may be made so low that the patient can do the fixation. Instead of turning off the fixation target, the light intensity of the fixation target is decreased as compared to the time of capture status adjustment. This makes it possible to fixate the eye even during inspection by the inspection set and smoothly shift to the next image capturing and also reduce the burden on the patient. Note that if the light intensity of the fixation target is made so low that the patient can do the fixation during the time from step S8 to step S17, the patient can recognize the completion and start of image capturing.

In step S13 to which the process advances when all the scanning patterns stored in the inspection set are completed, the screen display is switched from the confirmation screen 2000 to the capture screen 1000. After that, the inspection ends in step S14, and the fixation target 191 is turned off. Since the fixation target 191 in the on state fixates the eye to be inspected until the end of inspection, the operator can smoothly perform the inspection.

The procedure of image capturing according to this embodiment has been described above.

Figure 4B:
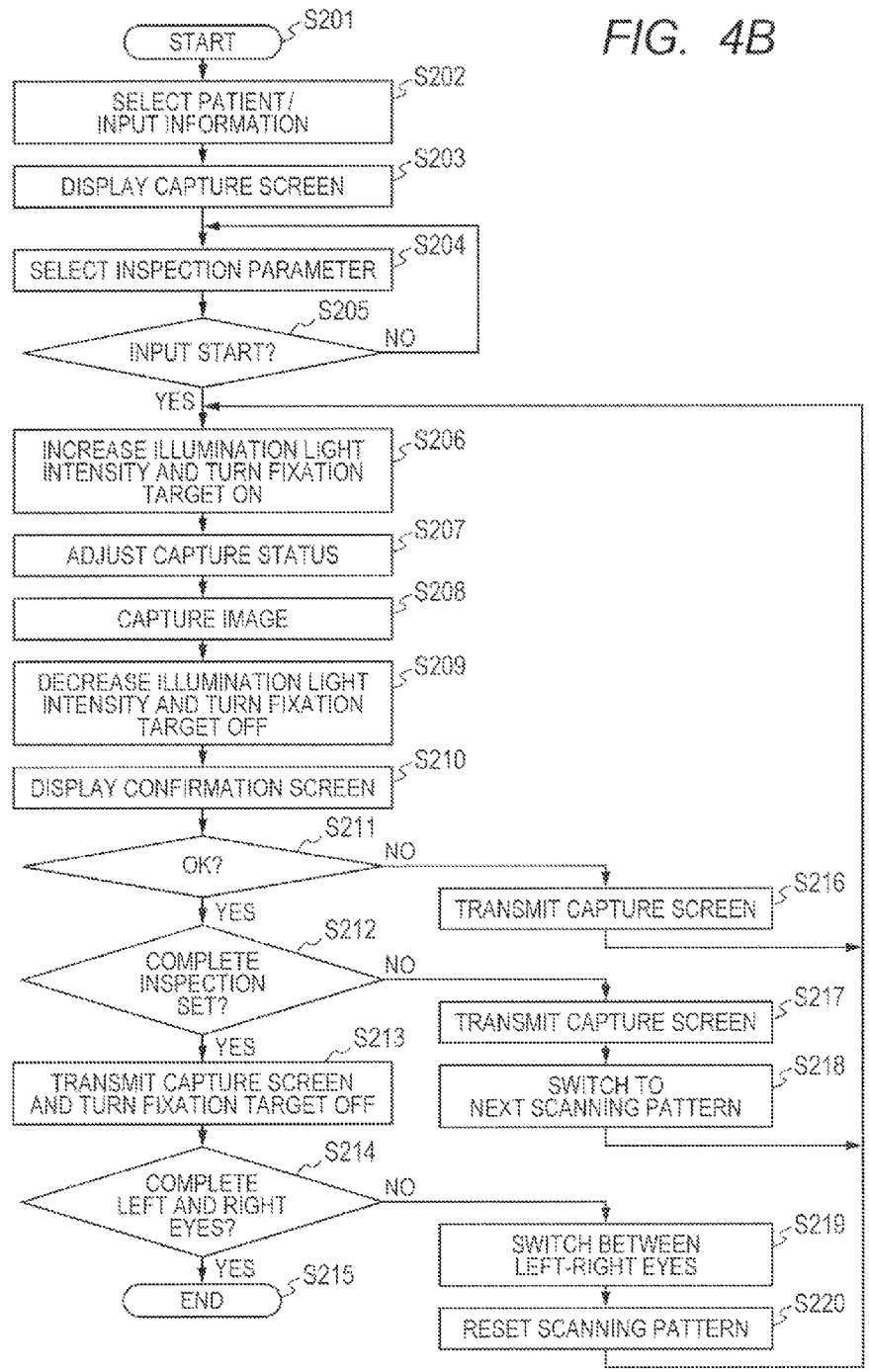

Modifications of the above-described procedure will be explained next with reference to FIGS. 4A and 4B.

FIG. 4A illustrates an operation procedure obtained by adding automatic adjustment to the above-described operation procedure. Steps S101 to S106 are the same as steps S1 to S6 described above, and a description thereof will be omitted.

In step S107 after the fixation target 191 is turned on to fixate the eye to be inspected, and the measuring light is increased up to the capture enable level, various kinds of adjustment are performed, based on the acquired anterior ocular observation image, two-dimensional fundus image, and tomographic image to obtain an optimum capture status. More specifically, the stage unit 950 is driven and controlled automatically based on the information of the anterior ocular observation image so that the inspection unit is located at an optimum position with respect so the eye to be inspected. In addition, the mirror 132-4 is automatically driven and controlled based on the information of the tomographic image to adjust the optical path length the reference light path. Simultaneously, the lenses 135-3 and 135-5 are automatically driven and controlled to focus the fundus image and the tomographic image. The apparatus state is automatically changed to a state optimum for image capturing of the eye to be inspected. After that, the process advances to step S108.

In step S108, the operator selects whether to capture an image in this adjusted state while viewing the image adjusted in step S107. To capture an image, the image capturing button 1003 displayed on the capture screen 1000 is selected using a mouse or the like, and the process advances to step S109.

On the other hand, when the operator views the image adjusted in step S107 and judges in step S108 that further adjustment is necessary, the process advances to step S116.

In step S116, the capture status is adjusted by The operation of the operator. More specifically, the operator adjusts the X and Y positions by clicking inside the anterior ocular observation screen 1101 while viewing the capture screen 1000. The operator also performs Z position adjustment, focusing adjustment, and coherence gate adjustment by sliding the sliders 1103, 1203, and 1302. If a capture enable state is obtained by the above-described manual adjustment, the image capturing instruction is input in step S108, and the process advances to step S109.

Processing from image capturing of step S109 to the end of step S115 (including steps S117 to S119) is same as the processing from step S9 to step S14 (including steps S15 to 517) in the above-described operation procedure, and a description thereof will be omitted. With the above-described procedure, along with an automatic increase in the illumination light intensity, the patient can be caused to fixate the eye during an imaging set while automatically performing adjustment. This makes it possible to reduce operation requests to the operator and improve the operability.

An operation procedure including left-right eye switching will be described next with reference to FIG. 4B.

Steps S201 to S212 (including steps S216 to S218) are the same as steps S1 to S12 (including steps S15 to S17) in the above-described operation procedure, and a description thereof will be omitted.

In this operation procedure, in step S214 after image capturing using the last scanning pattern of the inspection set is performed, and the capture screen is displayed, it is judged whether the inspection of both the left and right eyes has ended.

Upon judging in step S214 that the inspection of both the left and right eyes has not ended, that is, inspection of the eye on the opposite side of the eye that has been inspected so far is to be performed, the fixation target 191 is turned off, and the process advances to step S219.

In step S219, to align the inspection unit with respect to the eye on the opposite side of the eye that has been inspected, so far, the stage unit 950 is driven and controlled based on the standard eye position information stored in the personal computer 925 in advance. After that, the process advances to step S220.

In step S220, the scanning pattern is reset and returned to the initial state for the next inspection. This makes it possible to start inspection for the other eye to be inspected using the first scanning pattern of the inspection set selected in step S204. After that, the process returns to step S206 to automatically turn the fixation target 191 on to fixate the eye to be inspected and increase the illumination light, intensity.

When the process has advanced to step S214 in a state in which the inspection of both the left and right eyes has ended, the process advances to step S215 to end the inspection.

As described above, when the left and right eyes are automatically switched, the measurement time can be shortened, and the throughput can be improved.

In the above description, focus is placed only on the measuring light in the method of increasing/decreasing the intensity of light illuminating the patient. However, the present invention is not limited to this. For example, when the anterior ocular observation illumination light is increased/decreased at the same time as the increase/decrease of the measuring light, the intensity of light illuminating the patient can be further decreased. The illumination light intensity can further be decreased by increasing/decreasing the fundus observation illumination light as well. This will be explained in the second embodiment.

Second Embodiment

In the second embodiment, a form in which SLO is used to acquire a two-dimensional image will be described.

An optical system and an operation procedure according to the second embodiment will be described with reference to FIGS. 5A and 5B. Only the operation procedure and the changed points of the optical system will be explained here, and a description of the remaining parts will be omitted.

Figure 5A:
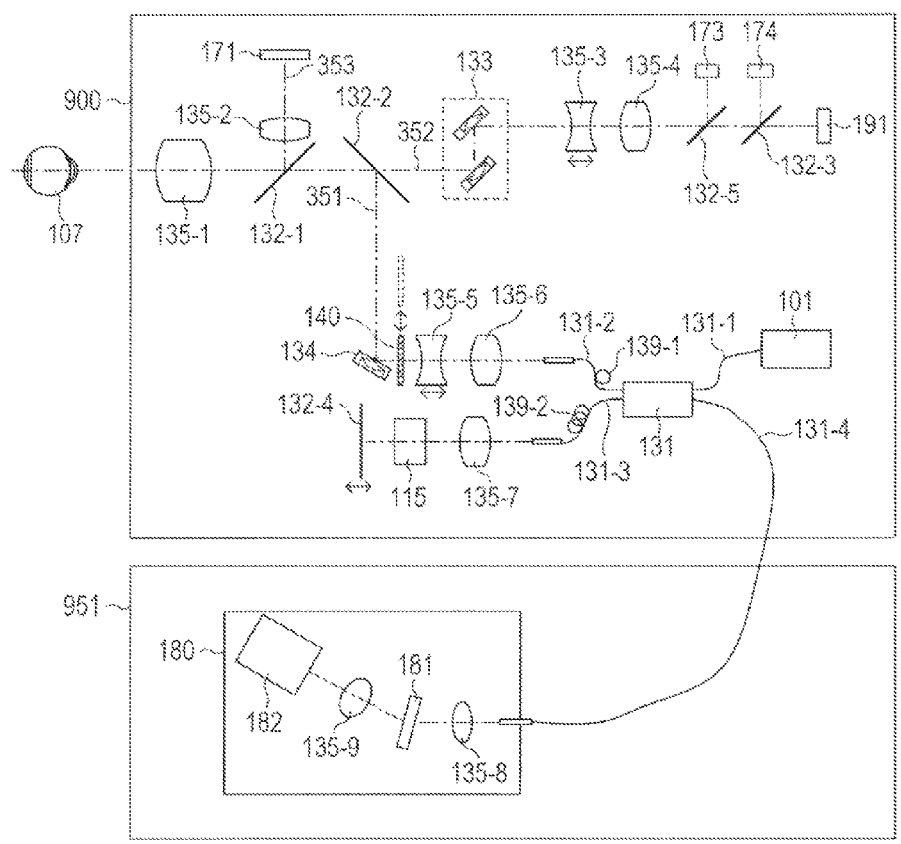
FIG. 5A as an explanatory view of an optical system according to the second embodiment.

FIG. 5A shows the optical system according to the second embodiment. Only points different from the first embodiment will be described here, and a description of the remaining parts will be omitted.

An optical path 352 includes a third dichroic mirror 132-3, lenses 135-3 and 135-4, and a fixation target 191, as in the first embodiment. In the second embodiment, the optical path 352 also includes an SLO light source 174, a mirror 132-5, a photodiode 173, and an SLO scanning unit 133. The SLO light source 174 emits light having a wavelength near 780 nm. The mirror 132-5 is formed from a prism on which a perforated mirror or a hollow mirror is deposited, and separates illumination light emitted by the SLO light source 174 and return light from the fundus. The photodiode 173 detects the return light from the fundus. The SLO scanning unit 133 scans light emitted by the SLO light source 174 on the fundus of an eye 107 to be inspected, and is formed from an X scanner that scans in the X direction and a Y scanner that scans an the Y direction. In this embodiment, the X scanner needs to perform high-speed scanning and is therefore formed from a polygon mirror. Note that in this embodiment, the SLO scanning unit 133 also functions as a fixation light scanning unit that scans fixation light on the eye to be inspected.

When the fundus of the eye to be inspected is observed using the above-described arrangement, a two-dimensional fundus image having a high contrast can be acquired using near infrared light.

The operation procedure according to the second embodiment will be described next with reference to FIG. 5B. Only steps S406 to S109 that are different from the first embodiment will be explained here, and a description of the remaining steps will be omitted.

In this operation procedure, in step S406, the fixation target 191 is turned on to fixate the eye to be inspected, and the intensity of measuring light to r acquiring a tomographic image is increased. At the same time, the intensity of illumination light (SLO light) for acquiring a two-dimensional fundus image is also increased. More specifically, the SLO scanner 133 is driven, and the intensity of light, emitted by the SLO light source 174 is controlled and increased.

In the step S407 to which the process advances after image capturing, the intensity of the measuring light is decreased, and at the same time, the intensity of the light for the two-dimensional image is also decreased. More specifically, the intensity of the light emitted by the SLO light source 174 is controlled and decreased. In addition, the fixation target 191 is blinked to notify the patient of the end of measurement. The patient may be notified by causing the fixation target 191 to not blink but reduce the light intensity or change the size or color. The SLO scanner 133 is stopped at an arbitrary position.

When the above-described arrangement and operation procedure are used, it is possible to provide an ophthalmologic apparatus capable of obtaining a two-dimensional observation image having a high contrast by SLO and decreasing the intensity of illumination light while causing the patient to fixate the eye during an inspection set.

Third Embodiment

Figure 6:
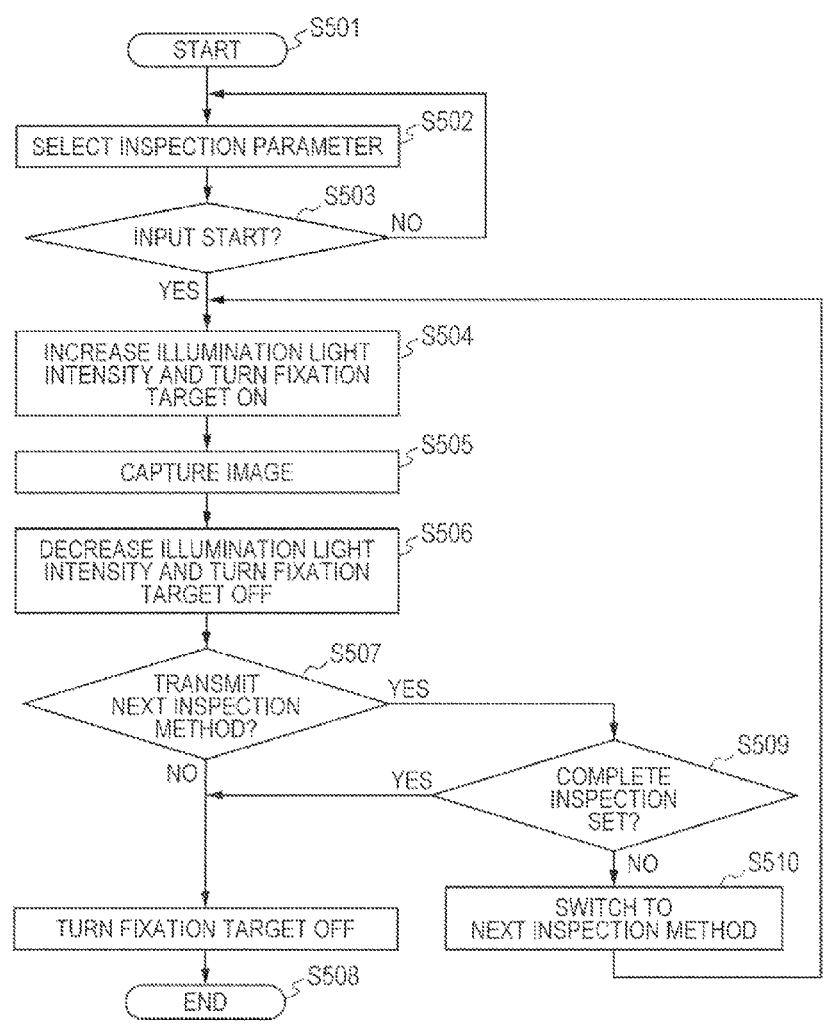
FIG. 6 is an explanatory view of an operation procedure according to the third embodiment.

In this embodiment, the intensity of measuring light is increased/decreased without screen transition. An operation procedure according to this embodiment will be described with reference to FIG. 6.

In step S501, inspection starts. Then, the process advances to step S502.

In step S502, the operator selects an inspection set appropriate for inspection of an object to be inspected. The inspection set stores a plurality of methods of acquiring different pieces of information from the object to be inspected in order. An example of the acquisition method is the above-described scanning pattern. When the object to be inspected is scanned using different scanning patterns, different pieces of information of the object to be inspected can be obtained. The inspection set can be selected using an input unit such as a button provided on an apparatus (not shown) in advance or by input from the above-described capture screen. After the inspection set selection by the operator in this step has ended, the process advances to step S503.

In step S503, the operator selects whether to increase the intensity of measuring light that illuminates the object to be inspected. It the intensity is not to be increased, a standby state is set. This selection can also be done using an input unit such as a button provided on an apparatus (not shown) in advance or by input from the above-described capture screen. After the operator has selected to increase the measuring light in this step, the process advances to step S504.

In step S504, a fixation target 191 is turned on to cause she patient to fixate the eye, and the intensity of the measuring light that illuminates the object to be inspected is increased. The tomographic information of the object to be inspected can thus be obtained. The method of increasing the intensity of the measuring light has been described in the first embodiment, and a description thereof will be omitted here. In addition, various kinds of adjustment of the imaging status, for example, alignment adjustment, focusing adjustment, and reference light path length adjustment may be performed using the acquired tomographic image of the object to be inspected. In this case, the instructions of the various kinds of adjustment can be input using an input unit such as a button provided on an apparatus (not shown) in advance or by input from the above-described capture screen.

The process advances to step S505 when the operator has manipulated an input unit such as an imaging button provided on the apparatus (not shown) in advance in the preceding step. The process may advance upon input from the above-described capture screen or automatically advance when the various kinds of adjustment are completed.

In step S505, the tomographic image is captured based on the acquisition method based on the inspection parameter set in step S502 and simultaneously saved in she storage device of a personal computer 925. After that, the process automatically advances to step S506.

In step S506, the intensity of the measuring light illuminating the object to be inspected is decreased. Since this can decrease the total intensity of the light illuminating the object to be inspected, a minimally invasive image capturing apparatus can be implemented. The method of decreasing the intensity of the measuring light has been described in the first embodiment, and a description thereof will be omitted here. After that, the process advances to step S507.

In step S507, the operator judges whether to transit to the next inspection method. Upon selecting to transit to the next inspection method, the process advances to step S509. Upon selecting not to transit, the process advances to step S508 to turn the fixation target 191 off. This selection can be done using an input unit such as a button provided on an apparatus (not shown) in advance or by input from the above-described confirmation screen. The process may automatically advance to the next step. Alternatively, for example, a timer for counting the time after image capturing may be provided in the personal computer 925, and the process may automatically advance to step S509 after the elapse of a predetermined, time from image capturing.

In step S509, it is automatically judged whether all the inspections by the plurality of acquisition methods preset in the inspection set have ended. If all the inspections have ended, the process advances to step S508 to turn the fixation target 191 off. On the other hand, if inspection by another acquisition method still remains, the process advances to step S510.

In step S510, the next acquisition method predetermined in the inspection set selected in step S502 is transferred to the personal computer 925 serving as a control unit, and the control unit prepares for the next inspection. After that, the process returns to step S504 to automatically increase the intensity of the measuring light illuminating the object to he inspected.

When the process has advanced up to step S508, the inspection ends.

When a plurality of inspections of the object to be inspected are performed using the above-described operation procedure, automatically switching the plurality of inspections and automatically increasing/decreasing the illumination light intensity while causing the patient to fixate the eye can be implemented without screen display.

As described above, according to the present invention, since no dedicated fixation optical system is used, an ophthalmologic apparatus having a simpler mechanism can be provided.

It is also possible to provide an ophthalmologic apparatus that presents the patient the shift of an inspection pattern in an inspection set by a simpler and Inexpensive mechanism. Furthermore, since the patient can automatically be caused to fixate the eye without illuminating the patient with unnecessary light, it is possible to provide an ophthalmologic apparatus capable of reducing burden on the patient.

Other Embodiments

The present invention is also implemented by executing the following processing. That is, software (program) that implements the functions of the above-described embodiments is supplied to the system or apparatus via a network or various kinds of storage media, and the computer (or CPU or MPU) of the system or apparatus reads out and executes the program.

While the present invention has been described with reference to exemplary embodiments, it is to be understood that the invention not limited to the disclosed exemplary embodiments. The scope of the following claims is to be accorded the broadest interpretation so as to encompass all such modifications and equivalent structures and functions.

This application claims the benefit of Japanese Patent Application No. 2012-189800, filed Aug. 30, 2012, which is hereby incorporated by reference herein in its entirety.

What is claimed is:

1. An ophthalmologic apparatus comprising:
a scanning unit configured to scan measuring light on an eye to be inspected based on a plurality of scanning conditions different from each other included within an inspection set, and execute measurement of the eye to be inspected;
a fixation unit configured to fixate the eye to be inspected by fixation light to a desired measurement position;
a determination unit configured to determine whether to continue the measurement of the eye to be inspected, after a completion of the measurement of the eye to be inspected under a first scanning condition included in the inspection set, under a second scanning condition next to the first scanning condition; and
a fixation target control unit configured to change the fixation light to measure the eye to be inspected under the second scanning condition when the determination unit has determined to continue the measurement of the eye to be inspected,
wherein the fixation target control unit causes the fixation light not to turn off after the completion of the measurement of the eye to be inspected under the first scanning condition and until the fixation light is changed by the fixation target control unit.

2. An apparatus according to claim 1, further comprising a scanning condition change unit configured to change a scanning condition of the measuring light of the scanning unit,
wherein when the scanning condition change unit has changed the scanning condition, and the determination unit has determined to continue the measurement of the eye to be inspected, the fixation target control unit changes the fixation light.

3. An apparatus according to claim 1, wherein the fixation target control unit causes the fixation unit to change an on position of the fixation light, as changing the fixation light.

4. An apparatus according to claim 1, further comprising an imaging unit configured to capture an image of the eye to be inspected obtained by scanning of the measuring light in the measurement.

5. An ophthalmologic apparatus comprising:
a scanning unit configured to scan measuring light on an eye to be inspected and executes measurement of the eye to be inspected;
a fixation unit configured to fixate the eye to be inspected to a desired measurement position by fixation light;
an inspection set unit configured to cause the scanning unit to execute the measurement based on measurement information representing an order of execution of a plurality of scanning conditions;
a determination unit configured to determine, after an end of the measurement under a first scanning condition, whether to start the measurement by the scanning unit under a second scanning condition next to the first scanning condition; and
a fixation target control unit configured to cause the fixation unit to fixate the eye to be inspected and execute first fixation line control, and when the determination unit has determined to start the measurement by the scanning unit under the second scanning condition next to the first scanning condition, cause the fixation unit to fixate the eye to be inspected and execute second fixation line control,
wherein the fixation target control unit causes the fixation light not to turn off after a completion of the measurement of the eye to be inspected under the first scanning condition and until the second fixation line control is started.

6. An apparatus according to claim 5, wherein the fixation target control unit comprises a fixation light scanning unit configured to scan the fixation light on the eye to be inspected.

7. A control method of an ophthalmologic apparatus comprising:
scanning measuring light on an eye to be inspected based on a plurality of scanning conditions different from each other included within an inspection set, and executing measurement of the eye to be inspected;
fixating the eye to be inspected by fixation light to a desired measurement position;
determining whether to continue the measurement of the eye to be inspected, after a completion of the measurement of the eye to be inspected under a first scanning condition included in the inspection set, under a second scanning condition next to the first scanning condition; and
changing the fixation light by a fixation target control unit to measure the eye to be inspected under the second scanning condition when it has been determined to continue the measurement of the eye to be inspected,
wherein the fixation target control unit causes the eye to be inspected to be fixated after the completion of the measurement of the eye to be inspected under the first scanning condition and until the fixation light is changed by the fixation target control unit.

8. An ophthalmologic apparatus comprising:
a scanning unit configured to scan measuring light on an eye to be inspected based on a plurality of scanning conditions different from each other included within an inspection set, and execute measurement of the eye to be inspected;
a fixation unit configured to fixate the eye to be inspected by fixation light to a desired measurement position;
a determination unit configured to determine whether to continue the measurement of the eye to be inspected, after a completion of the measurement of the eye to be inspected under a first scanning condition included in the inspection set, under a second scanning condition next to the first scanning condition; and
a fixation target control unit configured to change the fixation light to measure the eye to be inspected under the second scanning condition when the determination unit has determined to continue the measurement of the eye to be inspected,
wherein the fixation target control unit controls the fixation light so that the eye to be inspected is fixated after the completion of the measurement of the eye to be inspected under the first scanning condition and until the fixation light is changed by the fixation target control unit.

9. An ophthalmologic apparatus according to claim 8, further comprising an acquiring unit configured to acquire a tomographic image of the eye to be inspected based on the measuring light.

10. An ophthalmologic apparatus according to claim 9, wherein the first scanning condition includes a first scanning pattern, the second scanning condition includes a second scanning pattern, and each of the first scanning pattern and the second scanning pattern is one of a line scan, a cross line scan, a plural line scan, circle scan, and a radial scan.

11. An ophthalmologic apparatus according to claim 10, wherein the fixation target control unit causes the fixation light to be turned on or to be blinked after the completion of the measurement of the eye to be inspected under the first scanning condition and until the fixation light is changed by the fixation target control unit.

12. An ophthalmologic apparatus according to claim 9, wherein the fixation target control unit causes the fixation light to be turned on or to be blinked after the completion of the measurement of the eye to be inspected under the first scanning condition and until the fixation light is changed by the fixation target control unit.

13. An ophthalmologic apparatus according to claim 10 further comprising:
a memory configured to store the plurality of inspection sets; and
a selection unit configured to select an inspection set among the plurality of inspection sets.

14. An ophthalmologic apparatus according to claim 13, further comprising a display control unit configured to cause a display unit to display scanning patterns included in the inspection set selected by the selection unit.

15. An ophthalmologic apparatus according to claim 14, wherein the fixation target control unit causes the fixation light to be turned on or to be blinked after the completion of the measurement of the eye to be inspected under the first scanning condition and until the fixation light is changed by the fixation target control unit.

16. An ophthalmologic apparatus according to claim 13, wherein the fixation target control unit causes the fixation light to be turned on or to be blinked after the completion of the measurement of the eye to be inspected under the first scanning condition and until the fixation light is changed by the fixation target control unit.

17. An ophthalmologic apparatus according to claim 8, wherein the fixation target control unit changes an on-position of the fixation light as changing the fixation light.

18. An ophthalmologic apparatus according to claim 8, wherein the fixation target control unit causes the fixation light to be turned on or to be blinked after the completion of the measurement of the eye to be inspected under the first scanning condition and until the fixation light is changed by the fixation target control unit.

19. An ophthalmologic apparatus comprising:

a scanning unit configured to scan measuring light on an eye to be inspected based on a plurality of scanning conditions different from each other included within an inspection set, and execute measurement of the eye to be inspected;

a fixation unit configured to fixate the eye to be inspected by fixation light to a desired measurement position; and a fixation target control unit configured to change the fixation light to measure the eye to be inspected under a second scanning condition when the eye to be inspected is measured, after a completion of the measurement of the eye to be inspected under a first scanning condition included in the inspection set, under a second scanning condition next to the first scanning condition, wherein the fixation target control unit controls the fixation light so that the eye to be inspected is fixated after the completion of the measurement of the eye to be inspected under the first scanning condition and until the fixation light is changed by the fixation target control unit.

* * * * *